(12) United States Patent
Chappell et al.

(10) Patent No.: US 11,607,399 B2
(45) Date of Patent: *Mar. 21, 2023

(54) PHARMACEUTICAL FORMULATION FOR HISTONE DEACETYLASE INHIBITORS

(71) Applicant: Medivir AB, Huddinge (SE)

(72) Inventors: Todd W. Chappell, Alexandria, VA (US); Keith A. Johnson, Durham, NC (US)

(73) Assignee: Medivir AB

( * ) Notice: Subject to any disclaimer, the term of this patent is extended or adjusted under 35 U.S.C. 154(b) by 102 days.

This patent is subject to a terminal disclaimer.

(21) Appl. No.: 16/924,591

(22) Filed: Jul. 9, 2020

(65) Prior Publication Data

US 2021/0038555 A1 Feb. 11, 2021

Related U.S. Application Data

(60) Division of application No. 16/275,395, filed on Feb. 14, 2019, now abandoned, which is a division of application No. 15/637,979, filed on Jun. 29, 2017, now Pat. No. 10,258,595, which is a division of application No. 14/983,761, filed on Dec. 30, 2015, now abandoned, which is a continuation of application No. 13/878,994, filed as application No. PCT/US2011/056148 on Oct. 13, 2011, now Pat. No. 9,255,066.

(60) Provisional application No. 61/392,855, filed on Oct. 13, 2010.

(51) Int. Cl.

| | |
|---|---|
| *A61K 31/235* | (2006.01) |
| *A61K 9/00* | (2006.01) |
| *A61K 9/06* | (2006.01) |
| *A61K 31/165* | (2006.01) |
| *A61K 31/222* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/38* | (2006.01) |
| *C07C 259/06* | (2006.01) |

(52) U.S. Cl.
CPC .......... *A61K 31/235* (2013.01); *A61K 9/0014* (2013.01); *A61K 9/06* (2013.01); *A61K 31/165* (2013.01); *A61K 31/222* (2013.01); *A61K 47/02* (2013.01); *A61K 47/10* (2013.01); *A61K 47/12* (2013.01); *A61K 47/14* (2013.01); *A61K 47/38* (2013.01); *C07C 259/06* (2013.01)

(58) Field of Classification Search
CPC ...... A61K 31/235; A61K 9/0014; A61K 9/06; A61K 31/165; A61K 31/222; A61K 47/02; A61K 47/10; A61K 47/12; A61K 47/14; A61K 47/38; A61K 47/00; A61K 2121/00; C07C 259/06; A61P 17/00; A61P 17/06; A61P 17/10; A61P 17/14; A61P 35/00; A61P 35/02; A61P 43/00
See application file for complete search history.

(56) References Cited

U.S. PATENT DOCUMENTS

| | | | |
|---|---|---|---|
| 6,110,697 A | 8/2000 | Dulski et al. | |
| 6,376,508 B1 | 4/2002 | Li et al. | |
| 6,387,673 B1 | 5/2002 | Evans et al. | |
| 6,706,686 B2 | 3/2004 | Long et al. | |
| 6,706,762 B1 | 3/2004 | Evans et al. | |
| 6,809,118 B2 | 10/2004 | Chung | |
| 6,946,441 B2 | 9/2005 | Long et al. | |
| 7,229,963 B2 | 6/2007 | Sartorelli et al. | |
| 2008/0206159 A1 | 8/2008 | Tamarkin et al. | |
| 2014/0213620 A1 | 7/2014 | Bradner et al. | |

FOREIGN PATENT DOCUMENTS

| | | |
|---|---|---|
| CN | 101528679 A | 9/2009 |
| WO | 2007024574 A2 | 3/2007 |
| WO | 2007095584 A2 | 8/2007 |

OTHER PUBLICATIONS

2005—"Remington: The Science and Practice of Pharmacy," 21st Edition, pp. 880-881.
Nov. 16, 2006—Bradner, J. E. et al., "Design and Characterization of a Novel, Reverse Prodrug Histone Deacetylase Inhibitor for Cutaneous T-Cell Lymphoma," (Abstract), Blood, vol. 108, pp. 272B-273B, Database Biosis [Online] XP002667464.
Jul. 2, 2012—(PCT) International Search Report—App PCT/US2011/056148.
Apr. 16, 2013—(PCT) International Preliminary Report on Patentability and Written Opinion—App PCT/US2011/056148.

*Primary Examiner* — Kortney L. Klinkel
*Assistant Examiner* — Jason Deck
(74) *Attorney, Agent, or Firm* — Banner & Witcoff, Ltd.

(57) ABSTRACT

A pharmaceutical composition, comprising a therapeutically effective amount of an active pharmaceutical ingredient (API) compound represented by the following structural formula

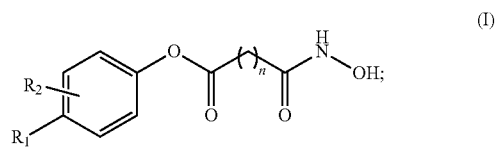

at least one acidifying agent; and a vehicle base comprising at least one pharmaceutically acceptable non-aqueous solvent. Values and preferred values of the variables in structural formula (I) are defined herein.

19 Claims, 1 Drawing Sheet

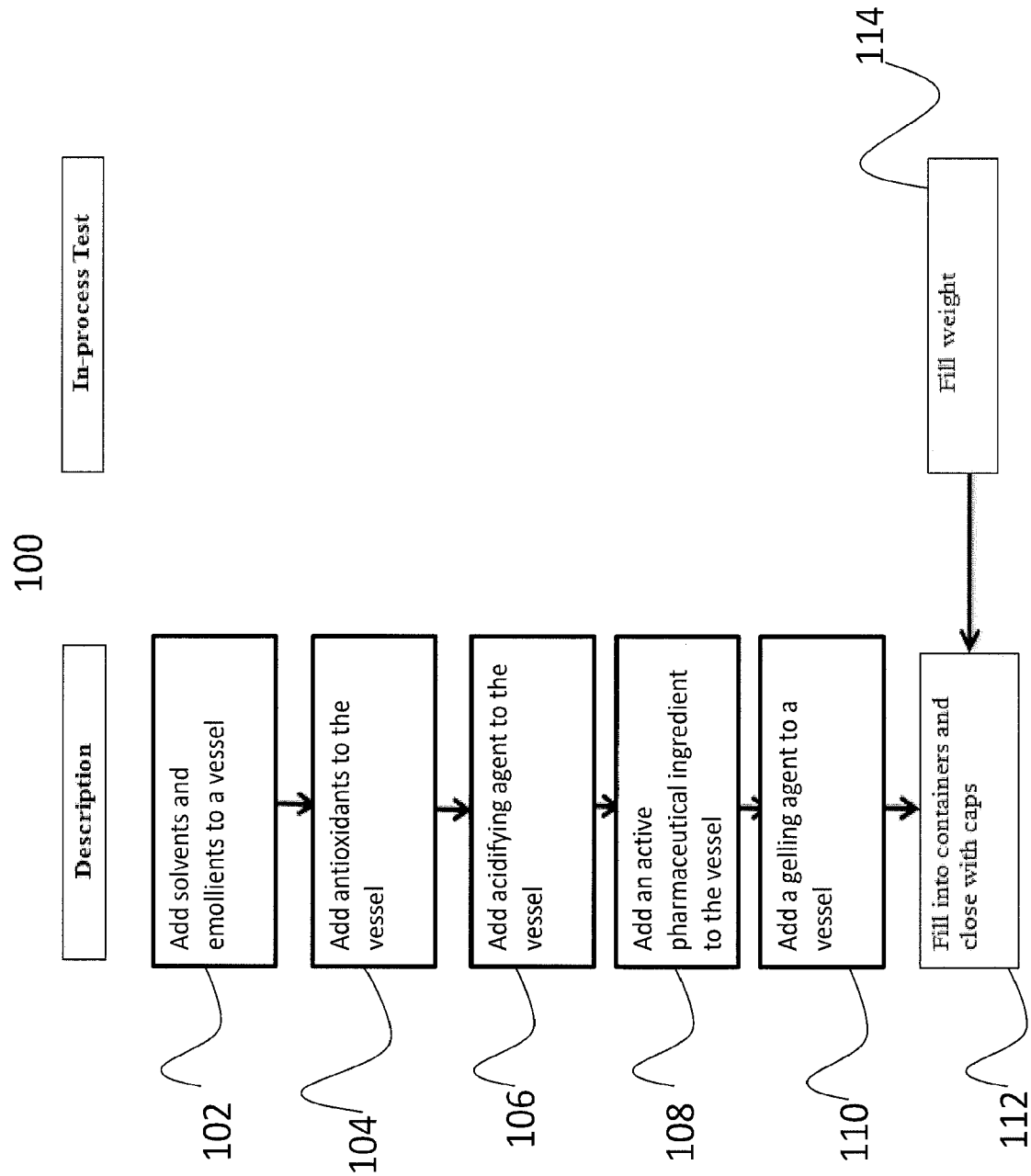

PHARMACEUTICAL FORMULATION FOR HISTONE DEACETYLASE INHIBITORS

RELATED APPLICATIONS

This application is a divisional of Ser. No. 16/275,395, filed Feb. 24, 2019, which is a division of Ser. No. 15/637,979, now U.S. Pat. No. 10,258,595, which is a divisional of Ser. No. 14/983,761, filed Dec. 30, 2015, now abandoned, which is a continuation of Ser. No. 13/878,994, now U.S. Pat. No. 9,255,066, which is a U.S. National Stage of PCT/US2011/056148, filed Oct. 13, 2011, which claims the benefit of Ser. No. 61/392,855, filed on Oct. 13, 2010; the entire contents of which are hereby incorporated by reference.

BACKGROUND OF THE INVENTION

Post-translational modification of proteins through acetylation and deacetylation of lysine residues has a critical role in regulating cellular functions, making histone deacetylase an attractive biological target, particularly for the treatment of cancer. For example, WO 2007/095584 describes small molecule inhibitors or histone deacetylase having an esterase sensitive ester linkage. The presence of the esterase-sensitive linker provides an inhibitor which can achieve high local concentrations and reduced systemic toxicity.

Some small molecules that include labile covalent bonds can be unstable in aqueous solvents. For example, the presence of an esterase-sensitive linker may present difficulties with respect to preparation of a suitable formulation. As such, a need exists for stable pharmaceutical compositions of histone deacetylase inhibitors when the inhibitor has labile covalent bonds, such as those described in WO 2007/095584.

SUMMARY OF THE INVENTION

The present invention relates to pharmaceutical composition comprising a histone deacetylase inhibitor, methods of using such a pharmaceutical composition and kits suitable for preparing such a pharmaceutical composition.

In one embodiment, the present invention is a pharmaceutical composition comprising a therapeutically effective amount of an active pharmaceutical ingredient (API) compound represented by the following structural formula

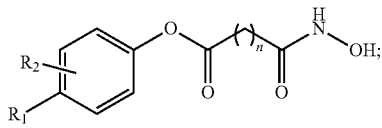

at least one acidifying agent; and a vehicle base comprising at least one pharmaceutically acceptable non-aqueous solvent. In structural formula (I), n is an integer from 0 to 15, $R_1$ and $R_2$ are each independently hydrogen, halogen, an aliphatic group, a heteroaliphatic group, an aryl, a heteroaryl; —$OR_A$; —$C(O)R_A$; —$C(O)N(R_A)_2$; —$CO_2R_A$; —CN; —SCN; —$SR_A$; —$SOR_A$; —$SO_2R_A$; —$NO_2$; —$N(R_A)_2$; —$NHR_A$; —$NR_AC(O)R_A$; or —$C(R_A)_3$; and wherein $R_A$ for each occurrence is, independently, a hydrogen, an aliphatic group, a heteroaliphatic group, an acyl moiety, an aryl moiety, a heteroaryl moiety, alkoxy; aryloxy; alkylthio, arylthio, amino, alkylamino, dialkylamino, heteroaryloxy, or heteroarylthio moiety.

In another embodiment, the present invention is a pharmaceutical composition. The composition comprises at least 0.01% by weight of an active pharmaceutical ingredient (API) compound represented by the following structural formula

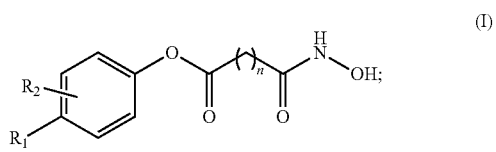

at least one acidifying agent; and at least one pharmaceutically acceptable non-aqueous solvent. Preferably, n is 6, $R_2$ is hydrogen and $R_1$ is —$C(O)OR_A$, $R_A$ is a $C_1$-$C_{12}$ alkyl; the at least one pharmaceutically acceptable non-aqueous solvent is a mixture of ethanol and propylene glycol; the at least one acidifying agent is selected from one or more of citric acid and phosphoric acid and the measured pH of the pharmaceutical composition is from about 3 to about 5 In a particular aspect of this embodiment, the pharmaceutical composition further optionally includes one or more of the following: at least one humectant selected from glycerin and hexylene glycol; at least one emollient selected from diisopropyl adipate and oleyl alcohol; at least one permeation enhancer selected from ethanol, propylene glycol, or oleyl alcohol; a hydroxypropylcellulose gelling agent; and a butylated hydroxytoluene as an antioxidant.

In another embodiment, the present invention is a method of treating a disorder in a subject in need thereof. The method comprises cutaneously administering to the subject a therapeutically effective amount of a pharmaceutical composition, wherein the disorder is selected from a proliferative disorder, an immune disorder and a skin disorder. The pharmaceutical composition useful for practicing the method of the present invention is described above.

In another embodiment, the present invention is a kit. The kit comprises a first container comprising an active pharmaceutical ingredient (API) compound represented by the following structural formula

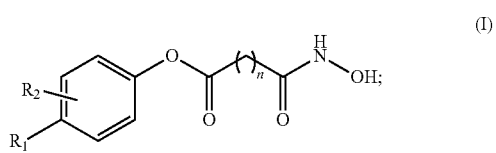

and
a second container comprising a vehicle base comprising at least one pharmaceutically acceptable non-aqueous solvent. Values and preferred values of the variables in structural formula (I) are defined herein below.

Pharmaceutical formulations of the present invention unexpectedly combine effective API delivery with extended shelf life at room temperature. A vehicle base comprising an acidified non-aqueous solvent contributes to the shelf life extension by retarding the degradation of API, for example by cleavage (e.g. by hydrolysis or solvolysis) of the labile covalent bonds of the API molecule.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

The FIGURE is a block diagram of one embodiment of the manufacturing process that can be employed to manufacture a pharmaceutical composition of the present invention.

DETAILED DESCRIPTION OF THE INVENTION

Histone deacetylase inhibitors such as those described in WO 2007/095584, incorporated herein by reference in its entirety, are small molecules that include labile covalent bonds that can be unstable in aqueous solvents. It has now been surprisingly discovered that stability and shelf-life of pharmaceutical formulations comprising the histone deacetylase inhibitors of WO 2007/095584 can be significantly enhanced by employing non-aqueous solvents that have been acidified.

In particular, some of the API compounds described in WO 2007/095584 include a labile bond (e.g. an ester bond), which hydrolyzes at room temperature. The mechanism of this hydrolysis may be either base-catalyzed or acid-catalyzed, depending on pH level. Traditional methods of retarding hydrolysis include either adjusting acidity (pH) of an aqueous solvent or substituting an aqueous solvent with a non-aqueous solvent. However, available experimental data indicates that neither one of these methods alone provides the desired API stability. Surprisingly, the combination of at least one non-aqueous solvent and at least one acidifying agent provides the desired API stability. Discovery of the suitability of this combination is unexpected. More particularly, because the rate of hydrolysis of a labile bond in different solvents as a function of acidity is unpredictable, the discovery of the existence of a combination of a solvent and an acidifying agent that provide for a sufficient stability of an API is also unpredictable and, therefore, unexpected.

Definitions of Terms

The term "aliphatic", as used herein, means non-aromatic group that consists solely of carbon and hydrogen and may optionally contain one or more units of unsaturation, e.g., double and/or triple bonds. An aliphatic group may be straight chained, branched or cyclic.

The term "heteroaliphatic," as used herein, means an aliphatic group in which one or more carbon atoms is replaced with a heteroatom, e.g., by O, N, S, Si, P or the like.

The term "alkyl", as used herein, unless otherwise indicated, means straight or branched saturated monovalent hydrocarbon radicals of formula $C_nH_{2n+1}$. In some embodiments, n is from 1 to 18. In other embodiments, n is from 1 to 12. Preferably, n is from 1 to 6. In some embodiments, n is 1-1000, for example, n is 1-100. Alkyl can optionally be substituted with —OH, —SH, halogen, amino, cyano, nitro, a $C_1$-$C_{12}$ alkyl, $C_1$-$C_{12}$ haloalkyl, $C_1$-$C_{12}$ alkoxy, $C_1$-$C_{12}$ haloalkoxy, $C_1$-$C_{12}$ alkyl sulfanyl, $C_2$-$C_{12}$ alkenyl, $C_2$-$C_{12}$ alkynyl group, an aryl or a heteroaryl. In addition, an alkyl can be substituted with =O, =S, =N-alkyl. Further examples of suitable substituents on an alkyl group include —R'OR, where each R and each R' is independently an alkyl, an aryl or a heteroaryl group. The term alkyl can also refer to cycloalkyl.

As used herein, an "alkenyl group," alone or as a part of a larger moiety (e.g., cycloalkene oxide), is preferably a straight chained or branched aliphatic group having one or more double bonds with 2 to about 12 carbon atoms, e.g., ethenyl, 1-propenyl, 1-butenyl, 2-butenyl, 2-methyl-1-propenyl, pentenyl, hexenyl, heptenyl or octenyl, or a cycloaliphatic group having one or more double bonds with 3 to about 12 carbon atoms. Exemplary substituents of an alkenyl group are described above with respect to alkyl.

As used herein, an "alkynyl" group, alone or as a part of a larger moiety, is preferably a straight chained or branched aliphatic group having one or more triple bonds with 2 to about 12 carbon atoms, e.g., ethynyl, 1-propynyl, 1-butynyl, 3-methyl-1-butynyl, 3,3-dimethyl-1-butynyl, pentynyl, hexynyl, heptynyl or octynyl, or a cycloaliphatic group having one or more triple bonds with 3 to about 12 carbon atoms. Exemplary substituents of an alkynyl group are described above with respect to alkyl.

The term "cycloalkyl", as used herein, means saturated cyclic hydrocarbons, i.e. compounds where all ring atoms are carbons. In some embodiments, a cycloalkyl comprises from 3 to 18 carbons. Preferably, a cycloalkyl comprises from 3 to 6 carbons. Examples of cycloalkyl include, but are not limited to, cyclopropyl, cyclobutyl, cyclopentyl, cyclohexyl, and cycloheptyl. Exemplary substituents of a cycloalkyl are described above with respect to alkyl.

The term "haloalkyl", as used herein, includes an alkyl substituted with one or more F, Cl Br, or I, wherein alkyl is defined above. Exemplary substituents of a haloalkyl are described above with respect to alkyl.

The terms "alkoxy," as used herein, means an "alkyl-O—" group, wherein alkyl is defined above. Examples of alkoxy group include methoxy or ethoxy groups. Exemplary substituents of an alkoxy are described above with respect to alkyl.

The terms "alkylthio," as used herein, means an "alkyl-S—" group, wherein alkyl is defined above. Examples of alkylthio group include $CH_3$—S— or $CH_3$—$CH_2$—S— groups. Exemplary substituents of an alkylthio group are described above with respect to alkyl.

The term "aryl," as used herein, refers to a carbocyclic aromatic group. Preferably, an aryl comprises from 6 to 18 carbons. Examples of aryl groups include, but are not limited to phenyl and naphthyl. Examples of aryl groups include optionally substituted groups such as phenyl, biphenyl, naphthyl, phenanthryl, anthracenyl, pyrenyl, fluoranthyl or fluorenyl. An aryl can be optionally substituted on a substitutable carbon atom. Examples of suitable substituents on an aryl include halogen, hydroxyl, cyano, nitro, C1-C12 alkyl, C2-C12 alkenyl or C2-C12 alkynyl, C1-C12 haloalkyl, C1-C12 alkoxy or haloalkoxy group, an aryloxy group, an arylamino group, an aryl, a heteroaryl group. In addition, an aryl can be substituted with =O, =S, =N-alkyl. Further examples of suitable substituents on an aryl group include —R'OR, where each R and each R' is independently an alkyl, an aryl or a heteroaryl group.

In some embodiments, a C6-C18 aryl is selected from the group consisting of phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. In some embodiments, a C6-C14 aryl selected from the group consisting of phenyl, naphthalene, anthracene, 1H-phenalene, tetracene, and pentacene.

The term "aryloxy," as used herein, means an "aryl-O—" group, wherein aryl is defined above. Examples of an aryloxy group include phenoxy or naphthoxy groups. Suitable substituents on an aryloxy group are as defined above with respect to an aryl group.

The term "arylthio," as used herein, means an "aryl-S—" group, wherein aryl is defined above. Examples of an aryloxy group include phenylthio or naphthylthio groups. Suitable substituents on an arylthio group are as defined above with respect to an aryl group.

The term "heteroaryl," as used herein, refers to aromatic groups containing one or more heteroatoms (O, S, or N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

In other embodiments, a 5-14-membered heteroaryl group selected from the group consisting of pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl.

The foregoing heteroaryl groups may be C-attached or N-attached (where such is possible). For instance, a group derived from pyrrole may be pyrrol-1-yl (N-attached) or pyrrol-3-yl (C-attached).

The term "(hetero)arylthio," as used herein, means an "(hetero)aryl-S—" group, wherein aryl is defined above. Examples of an arylthio group include phenylthio or naphthylthio groups.

Suitable substituents for heteroaryl are as defined above with respect to aryl group.

In some embodiments, suitable substituents for a substitutable carbon atom in an aryl, a heteroaryl or an aryl portion of an arylalkenyl include halogen, hydroxyl, C1-C12 alkyl, C2-C12 alkenyl or C2-C12 alkynyl group, C1-C12 alkoxy, aryloxy group, arylamino group and C1-C12 haloalkyl.

In the context of the present invention, an amino group may be a primary (—NH$_2$), secondary (—NHR$_p$), or tertiary (—NR$_p$R$_q$), wherein R$_p$ and R$_q$ may be any of the alkyl, alkenyl, alkynyl, alkoxy, cycloalkyl, cycloalkoxy, aryl, heteroaryl, and a bicyclic carbocyclic group. A (di)alkylamino group is an instance of an amino group substituted with one or two alkyls.

A "trialkylamino" group is a group —N$^+$(R$_t$)$_3$, wherein R$_t$ is an alkyl, as defined above.

As used herein, the term "acyl" refers to alkanoyl, i.e. a n alkyl-C(O)—, where "alkyl" is defined above.

The term (hetero)arylamine, as used herein, means an "(hetero)aryl-NH—", an "(hetero)aryl-N(alkyl)-", or an "((hetero)aryl)$_2$-N—" groups, wherein (hetero)aryl and alkyl are defined above.

A "humectant," as used herein, is an excipient that can increase the water level in the upper layers of the skin. Examples of humectants approved for use in topical drug products by the FDA include, but are not limited to, the following: hexylene glycol, propylene glycol, sorbitol, lactic acid, sodium lactate, methyl gluceth-10, methyl gluceth-20, and polyethylene glycols.

An "emollients," as used herein, is an excipient that can improve skin feel by softening, lubricating, and refatting the skin. Emollients may also improve the barrier function of skin and reduce water evaporation. Examples of emollients approved for use in topical drug products by the United States Food and Drug Administration (FDA) include, but are not limited to, the following: diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plaint oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglyerides, dimethicone, and cyclomethicone.

An "acidifying agent," as used herein, refers to a chemical compound that alone or in combination with other compounds can be used to acidify a vehicle base of a pharmaceutical composition comprising a non-aqueous solvent. An acceptable acidifying agent for a topical formulation is an acid with a pKa of 9.5 or less, more preferably having a pKa of 7.0 or less, most preferably having a pKa of 5.0 or less. Examples of acidifying agents approved for use in topical drug products by the FDA include, but are not limited to: acetic acid, dehydro acetic acid, ascorbic acid, benzoic acid, boric acid, citric acid, edetic acid, hydrochloric acid, isostearic acid, stearic acid, lactic acid, nitric acid, oleic acid, phosphoric acid, sorbic acid, sulfuric acid, tartaric acid, and undecylenic acid.

A "nonaqueous solvent," as used herein, is a solvent other than water. Examples of nonaqueous solvents approved for use in topical drug products by the FDA include, but are not limited to: alcohol (ethanol), acetone, benzyl alcohol, diethylene glycol monoethyl ether, glycerin, hexylene glycol, isoproypl alcohol, polyethylene glycols, methoxypolyethylene glycols, diethyl sebacate, dimethyl isosorbide, propylene carbonate, and dimethyl sulfoxide. Many emollients that are liquid at room temperature can also be used as solvents. These include, but are not limited to: diisopropyl adipate, isopropyl myristate, vegetable/plant oils, mineral oil, and isopropyl palmitate.

An "antioxidant," as used herein, is a substance that inhibits oxidation of chemical compounds. Examples of typical antioxidants include alpha tocopherol (all isomers), beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate. The chemical compounds protected from oxidation by an antioxidant include active pharmaceutical ingredients (API) and excipients containing moieties susceptible to oxidation.

A "gelling agent," as used herein, is a compound that thickens (i.e. increases the viscosity of) a formulation. Examples are hydroxypropylcelluloses, carbomer, hydroxyethylcelluloses, carboxymethylcelluloses, xanthan gum, guar gum, chitosan, polyvinyl alcohol, povidone, carrageenan, methyl cellulose, hydroxypropyl methyl cellulose, fatty alcohols, cetyl alcohol, stearyl alcohol, cetostearyl alcohol, and myristyl alcohol. In a particular embodiment, the gelling agent is a pharmaceutical grade hydroxypropylcellulose Klucel® MF ("Klucel MF PH"), available from Hercules Incorporated of Wilmington Del., under the catalog number 494-9.

A "skin permeation enhancer," as used herein, is a compound that improves absorption of a pharmaceutically active ingredient through a cutaneous membrane, e.g. skin.

"Measured pH," as used herein, is the acidity of an aliquot of a pharmaceutical composition of the present invention as defined herein, measured by diluting the aliquot with water to about 10% by volume.

As used herein, the term "therapeutically effective amount" refers to an amount of the API which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of compound administered to a subject will depend on the type and severity of the disease or condition and on the characteristics of the subject, such as general health, age, sex, body weight and tolerance to drugs. It will also depend on the degree, severity and type of the disorder being treated. The skilled artisan will be able to determine appropriate dosages depending on these and other factors. When co-administered with other agents, e.g., when co-administered with an anti-proliferative agent, a "therapeutically effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of one or more pharmaceutical compositions of the present invention. In specific embodiments, the terms "treat", "treatment" and "treating" refer to the amelioration of at least one measurable physical parameter being treated. For example, for a proliferative disorder, such parameters can include growth of a tumor, not necessarily discernible by the patient. In other embodiments the terms "treat", "treatment" and "treating" refer to the inhibition of the progression of a disorder being treated, either physically by, e.g., stabilization of a discernible symptom, physiologically by, e.g., stabilization of a physical parameter, or both. In the embodiments in which the disorder being treated is a proliferative disorder, the terms "treat", "treatment" and "treating" can refer to the reduction or stabilization of cancerous cell count.

An "ointment," as used herein, is a semisolid dosage form, usually containing less than 20% water and volatiles and more than 50% hydrocarbons, waxes, or polyols as the vehicle. This dosage form is generally for external application to the skin or mucous membranes.

"Semisolid," as used herein refers to the aggregate state of the matter that is not pourable; it does not flow or conform to its container at room temperature; it does not flow at low shear stress and generally exhibits plastic flow behavior.

A "gel," as used herein, is a semisolid dosage form that contains a gelling agent to thicken to a solution or fine particle dispersion. Thickening the formulation aids in application to a specific site on the body. A gel may contain suspended particles.

"Fine particle dispersion," as used herein, is a system in which fine particles of (i.e. typically less than 10-50 μm) are distributed uniformly throughout a liquid.

A "foam," as used herein, is a dosage form containing gas bubbles dispersed in a liquid that contains less than 50% water, and in a particular embodiment, no water.

Pharmaceutical Compositions

In one embodiment, the present invention is a pharmaceutical composition, comprising a therapeutically effective amount of an active pharmaceutical ingredient (API) compound represented by the following structural formula

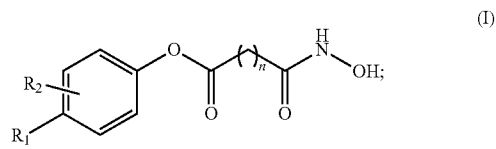

at least one acidifying agent and a vehicle base comprising at least one pharmaceutically acceptable non-aqueous solvent. In structural formula (I), n is an integer from 0 to 15, $R_1$ and $R_2$ are each independently hydrogen, halogen, an aliphatic group, a heteroaliphatic group, an aryl, a heteroaryl; —$OR_A$; —$C(O)R_A$; —$C(O)N(R_A)_2$; —$CO_2R_A$; —CN; —SCN; —$SR_A$; —$SOR_A$; —$SO_2R_A$; —$NO_2$; —$N(R_A)_2$; —$NHR_A$; —$NR_AC(O)R_A$; or —$C(R_A)_3$, wherein $R_A$ for each occurrence is, independently, a hydrogen, an aliphatic group, a heteroaliphatic group, an acyl moiety, an aryl moiety, a heteroaryl moiety, alkoxy; aryloxy; alkylthio, arylthio, amino, alkylamino, dialkylamino, heteroaryloxy, or heteroarylthio moiety.

In some embodiments, in structural formula (I), n is 5, 6 or 7, preferably, n is 6. Values and preferred values of the remainder of the variable are as defined above with respect to structural formula (I).

In other embodiments, in structural formula (I), $R_2$ is hydrogen and $R_1$ is selected from a halogen, —$OR_A$, $N(R_A)_2$, —$NHR_A$, —$C_1$-$C_6$ alkyl, —$C(O)R_A$, —$C(O)OR_A$, —$C(O)N(R_A)_2$, —$C(O)NH_2$, —CHO and —$NHC(O)R_A$. Values and preferred values of the remainder of the variable are as defined above with respect to structural formula (I). Preferably, $R_A$ is hydrogen or a $C_1$-$C_{12}$ alkyl. Values and preferred values of the remainder of the variable are as defined above with respect to structural formula (I).

In other embodiments, in structural formula (I), n is 6, $R_2$ is hydrogen and $R_1$ is —$C(O)OR_A$, and $R_A$ is a $C_1$-$C_{12}$ alkyl. Values and preferred values of the remainder of the variable are as defined above with respect to structural formula (I).

In some embodiments, at least one acidifying agent is selected from the groups consisting of acetic acid, dehydro acetic acid, ascorbic acid, benzoic acid, boric acid, citric acid, edetic acid, hydrochloric acid, isostearic acid, stearic acid, lactic acid, nitric acid, oleic acid, phosphoric acid, sorbic acid, sulfuric acid, tartaric acid, undecylenic acid, fumaric acid, malic acid, maleic acid, benzene sulfonic acid, cyclamic acid, diatrizoic acid, deoxycholic acid, gentisic acid, glucuronic acid, glutamic acid, and succinic acid. In a particular embodiment, at least one acidifying agent is selected from one or more of citric acid, acetic acid, and phosphoric acid.

In some embodiments, semi-polar non-aqueous solvents are preferred (e.g., miscible with water such as ethanol, propylene glycol). In other embodiments, at least one pharmaceutically acceptable non-aqueous solvent is selected from the groups consisting of ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate. In a particular embodiment, at least one pharmaceutically acceptable non-aqueous solvent is selected from ethanol, benzyl alcohol, propylene glycol, 2-(2-ethoxyethoxy) ethanol, hexylene glycol and diisopropyl adipate.

In some embodiments, a pharmaceutical composition of the present invention further includes at least one humectant. At least one humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols. In a particular embodiment, at least one humectant is selected from glycerin and hexylene glycol.

In some embodiments, the pharmaceutical composition of the present invention further includes at least one emollient. In some embodiments, at least one emollient is selected from the groups consisting of diisopropyl adipate, isopropyl myristate, isopropyl palmitate, cetearyl octonoate, isopropyl isostearate, myristyl lactate, octyldodecanol, oleyl alcohol, a mineral oil, petrolatum, a vegetable oil, PPG-15 stearyl ether, PEG-4 dilaurate, lecithin, lanolin, lanolin alcohol, polyoxyl 75 lanolin, cholesterol, cetyl esters wax, cetostearyl alcohol, glyceryl monostearate, triglycerides of capric and caprylic acids, dimethicone, and cyclomethicone. In a particular embodiment, at least one emollient is selected from diisopropyl adipate and oleyl alcohol.

In particular embodiments, the pharmaceutical composition of the present invention includes at least one humectant and at least one emollient. Values and preferred values of humectants and emollients are listed above. In a particular embodiment, at least one humectant is selected from one or more of glycerin and hexylene glycol and wherein the at least one emollient is selected from diisopropyl adipate and oleyl alcohol.

In some embodiments, the pharmaceutical composition of the present invention further includes at least one skin permeation enhancer. Suitable skin permeation enhancers include, but are not limited to, dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5 carboxylic acid, propylene glycol, ethanol, isopropanol, oleic acid, laurocapram (Azone), limonene, cineole, diethyl-m-toluamide (DEET), sodium dodecylsulfate, trimethyl phosphine oxide, tetrahydrofurfuryl alcohol, glycerol monolaurate, methyl oleate, propylene glycol monolaurate, and oleyl alcohol. In a specific aspect, at least one permeation enhancer is selected from oleyl alcohol, propylene glycol and ethanol.

In some embodiments, the pharmaceutical composition of the present invention further includes at least one gelling agent. In particular embodiments, gelling agents are neutral polymers that thicken at low pH, such as cellulose-based polymers, for example hydroxypropylcellulose. In particular embodiments, at least one gelling agents is selected from hydroxypropylcellulose, carbomer, hydroxyethylcellulose, carboxymethylcellulose, xanthan gum, guar gum, chitosan, polyvinyl alcohol, povidone, carrageenan, methyl cellulose, hydroxypropyl methyl cellulose, fatty alcohols, cetyl alcohol, stearyl alcohol, cetostearyl alcohol, and myristyl alcohol. In a particular embodiment, at least one gelling agent is a hydroxypropylcellulose such as Klucel MF PH.

In some embodiments, the pharmaceutical composition of the present invention further includes at least one antioxidant. In a particular embodiment, the antioxidant is selected from the groups consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate. In a particular embodiment, the antioxidant is the butylated hydroxytoluene (BHT).

In various embodiments, the pharmaceutical composition of the present invention comprises at least 0.01% by weight of the API. In some embodiments, the pharmaceutical composition of the present invention comprises from about 0.01% to about 15% by weight of the API. In other embodiments, the pharmaceutical composition of the present invention comprises at least about 0.1% by weight of the API, alternatively—at least 0.5% by weight of the API. For example, the pharmaceutical composition of the present invention comprises, by weight, at least about 0.01%, 0.02%, 0.03%, 0.04%, 0.05%, 0.06%, 0.07%, 0.08%, 0.09%, 0.1%, 0.1%, 0.2%, 0.3%, 0.4%, 0.5%, 0.6%, 0.7%, 0.8%, 0.9%, 1.0%, 1.5%, 2%, 2.5%, 3%, 3.5%, 4%, 4.5% or 5% of the API. In certain embodiments, the pharmaceutical composition of the present invention comprises at least about 10% by weight of the API.

In various embodiments, the measured pH of the pharmaceutical composition of the present invention is about 7. In other embodiments, the measured pH if the pharmaceutical composition of the present invention is from about 3 to about 6. In a particular embodiment, the measured pH is from about 3 to about 5.

An example of a pharmaceutical composition of the present invention, is a pharmaceutical composition as defined herein above, comprising at least 0.01% by weight of the API, wherein the vehicle base comprises a mixture of ethanol and propylene glycol, and wherein the measured pH of the pharmaceutical composition is from about 3 to 5. In a particular embodiment, the at least one acidifying agent is selected from one or more of citric acid and phosphoric acid. In some embodiments, the pharmaceutical composition further includes at least one humectant selected from one of more of glycerin and hexylene glycol. In other embodiment, the pharmaceutical composition further includes at least one emollient selected from one or more of diisopropyl adipate and oleyl alcohol. In a particular embodiment, the pharmaceutical composition further includes at least one permeation enhancer selected from one or more of oleyl alcohol, propylene glycol and ethanol. In further embodiments, the pharmaceutical composition further includes a hydroxypropylcellulose gelling agent such as Klucel MF PH.

In another example, a pharmaceutical composition of the present invention comprises at least 0.01% by weight (e.g., 0.01%, 0.02%, 0.03%, 0.04%, 0.05%, 0.06%, 0.07%, 0.08%, 0.09%, 0.1%, 0.1%, 0.2%, 0.3%, 0.4%, 0.5%, 0.6%, 0.7%, 0.8%, 0.9%, 1.0%, 1.5%, 2%, 2.5%, 3%, 3.5%, 4%, 4.5% or 5%) of an active pharmaceutical ingredient (API) compound represented by the following structural formula

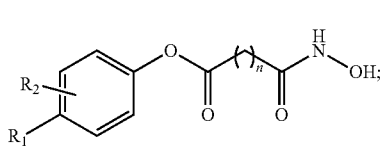

wherein n is 6, $R_2$ is hydrogen and $R_1$ is —C(O)O$R_A$, $R_A$ is a $C_1$-$C_{12}$ alkyl. The pharmaceutical composition can further include at least one acidifying agent, and at least one pharmaceutically acceptable non-aqueous solvent, the at least one pharmaceutically acceptable non-aqueous solvent is a mixture of ethanol and propylene glycol, the at least one acidifying agent is selected from one or more of citric acid and phosphoric acid and the measured pH of the pharmaceutical composition is from about 3 to about 5. The pharmaceutical composition can further include at least one humectant selected from one of more of glycerin and hexylene glycol; at least one emollient selected from one or more of diisopropyl adipate and oleyl alcohol; at least one permeation enhancer selected from one or more of oleyl alcohol, propylene glycol and ethanol; a hydroxypropylcellulose gelling agent such as Klucel MF PH; and a butylated hydroxytoluene as an antioxidant.

In a particular embodiment, the pharmaceutical composition of the present invention comprises the API is a compound represented by the following structural formula

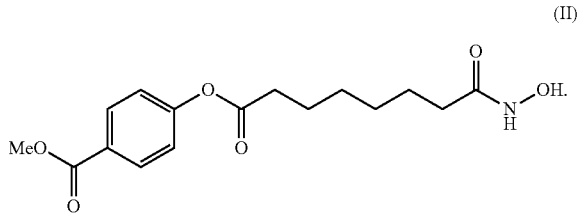 [SMILES: COC(=O)c1ccc(OC(=O)CCCCCCC(=O)NO)cc1]

In the above-described compositions of the present invention, the amount of a pharmaceutically acceptable non-aqueous solvent is the amount suitable to bring the composition to the desirable volume and/or weight. For example, on the weight per weight basis (% w/w), the amount of one or more solvents is from about 5% to about 99.9%. For example, the amount of one or more solvents can be 5%, 10%, 15%, 20%, 25%, 30%, 35%, 40%, 50%, 55%, 60%, 65%, 70%, 75%, 80%, 85%, 90%, 95%, or 99%. In other embodiments, on the weight per weight basis (% w/w), the amount of one or more humectants is, for example, from about 5% to about 50%, e.g. 5%, 10%, 15%, 20%, 25%, 30%, 35%, 40%, 50%. In other embodiments, on the weight per weight basis (% w/w), the amount of one or more emollients is, for example, from about 5% to about 50%, e.g. 5%, 10%, 15%, 20%, 25%, 30%, 35%, 40%, 50%. In other embodiments, on the weight per weight basis (% w/w), the amount of one or more antioxidants is, for example, from about 0.01% to about 5%, e.g. 0.01%, 0.05, 0.1%, 0.15%. 0.2%, 0.5%, 1.0%, 1.5%, 2.0%, 2.5%, 3.0%, 3.5%, 4.0%, or 5.0%. In other embodiments, on the weight per weight basis (% w/w), the amount of one or more acidifying agents is, for example, from about 0.01% to about 5.0%, e.g. 0.01%, 0.05, 0.1%, 0.15%. 0.2%, 0.5%, 1.0%, 1.5%, 2.0%, 2.5%, 3.0%, 3.5%, 4.0%, or 5.0%. In other embodiments, on the weight per weight basis (% w/w), the amount of one or more gelling agents is, for example, from about 0.5% to about 5.0%, e.g. 0.5%, 1.0%, 1.5%, 2.0%, 2.5%, 3.0%, 3.5%, 4.0%, or 5.0%.

Transdermal, topical, and mucosal dosage forms of the invention include, but are not limited to, ophthalmic and otic solutions, sprays, foams, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. See, e.g., Remington's Pharmaceutical Sciences (1980 & 1990) 16th and 18th eds., Mack Publishing, Easton, Pa.

Depending on the specific tissue to be treated, additional components may be used prior to, in conjunction with, or subsequent to treatment with active ingredients of the invention. For example, penetration enhancers can be used to assist in delivering the active ingredients to the tissue.

Different salts, hydrates or solvates of the active ingredients can be used to further adjust the properties of the resulting composition.

In a particular embodiment, pharmaceutical compositions of the present invention can be formulated as non-aqueous ointments, non-aqueous gels or non-aqueous foams.

Methods of Treatment

In some embodiments, the present invention is a method of treating a proliferative disorder, an immune disorder and a skin disorder in a subject in need thereof. The method comprises cutaneously administering to the subject a therapeutically effective amount of a pharmaceutical composition. The pharmaceutical composition comprises a pharmaceutically effective amount of an active pharmaceutical ingredient (API) compound represented by the following structural formula

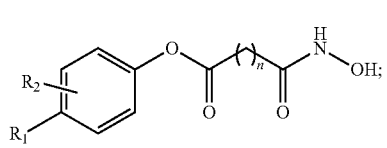

at least one acidifying agent, and at least one pharmaceutically acceptable non-aqueous solvent. The values and preferred values of the variables in structural formula (I) are as defined hereinabove. Particular and optional components and ingredients of pharmaceutical compositions useful in treating a proliferative disorder, an immune disorder and a skin disorder according to the methods of the present invention have also been described above.

In some embodiments, the present invention is a method of treating a selected from a disorder selected from the group consisting of cutaneous T cell lymphoma, a skin cancer, a benign skin growth, acne, psoriasis, dermatitis, actinic keratosis, basal cell carcinoma, neurofibromatosis, a leukemia, a malignant melanoma, hair loss, and skin hyperpigmentation. In a particular embodiment, the disorder is selected from cutaneous T-cell lymphoma, neurofibromatosis, actinic keratosis, acne, basal cell carcinoma, psoriasis, hair loss, skin pigmentation, and dermatitis.

Kits Comprising Pharmaceutical Compositions of the Present Invention

In some embodiments, the present invention is a kit, comprising a first container and a second container. The first container comprises an active pharmaceutical ingredient (API) represented by the following structural formula

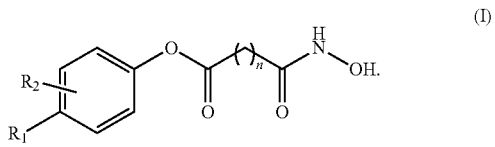

Values and preferred values of the variables in structural formula (I) are defined hereinabove. The second container comprises a vehicle base. The vehicle base includes at least one pharmaceutically acceptable non-aqueous solvent and at least one acidifying agent. Particular pharmaceutically acceptable non-aqueous solvent and acidifying agents are defined hereinabove.

In a particular embodiment, the first container comprises a therapeutically effective amount of the API.

In various embodiments, the kit can further include one or more of the following components: at least one gelling agent, at least one humectant, at least one emollient, at least one skin permeation enhancer, and at least one antioxidant. Suitable gelling agents, humectants, emollients, skin permeation enhancers and antioxidants are defined hereinabove.

In some embodiments, the kit further includes a third container comprising at least one gelling agent.

In some embodiments, the second container comprises ethanol, benzyl alcohol, and citric acid. In other embodiments, the third container further comprises propylene glycol, hexylene glycol, glycerin, diisopropyl adipate, oleyl alcohol, and butylated hydroxytoluene. In a particular embodiment, the third container further comprises propylene glycol, hexylene glycol, glycerin, diisopropyl adipate, oleyl alcohol, and butylated hydroxytoluene.

Any embodiment of the kit can further include instructions for the use of such kit. In some embodiments, the instructions include the steps of adding the content of the first container to the second container. In other embodiments, the instructions include the steps of blending the contents of the first, the second and the third containers.

Referring to the FIGURE, one example of a manufacturing process that can be employed to produce a pharmaceutical composition of the present invention is process 100. In step 102, solvents and emollients are added to a vessel. In particular embodiments, solvents and emollients are mixed to uniformity. In step 104, one or more antioxidants are added to the mixture. In a particular embodiment, butylated hydroxytoluene is added to the mixture and dissolved. In step 106, an acidifying agent is added to the vessel. In a particular embodiment, an anhydrous citric acid is added to the mixture. In step 108, an API is added to the mixture. In step 110, a gelling agent is added to the vessel. In a particular embodiment, Klucel MF PH is added to the mixture. In step 112, the mixture is aliquoted into desirable containers. Optionally, in step 114, fill weight of each container is checked for accuracy.

EXEMPLIFICATION

Example 1

Stability of Pharmaceutical Formulations of the Present Invention

Materials and Methods

API used was the compound of structural formula (II). All excipients used are listed in the United States Pharmacopeia-National Fromulary (USP/NF). Water and acetonitrile for HPLC analysis were HPLC grade. An Orion 710A+ meter with a Ross Ultra electrode (Thermo Electron Corp.) was used to measure pH. The samples were diluted $\frac{1}{10}$ prior to pH measurement to minimize junction potential errors in the measurement. Viscosity (at 20±1° C.) was measured with a Brookfield LVF viscometer at 12 rpm using a #25 spindle and 13R sample holder. Since the samples were stored at different temperatures, they were allowed to equilibrate at the viscosity measurement temperature for at least 12 hours. HPLC analysis was performed using an HP 1050 system equipped with a variable wavelength UV/Vis detector. A gradient HPLC method is summarized in Table 1.

TABLE 1

| Column | ACE 5 micron C18 4.6 × 150 mm |
|---|---|
| Mobile Phase A | 10% ACN/90%, 0.2% PCA |
| Mobile Phase B | 80% ACN/20%, 0.2% PCA |
| Gradient | 0.0 mm. 100% A |
|  | 20.0 mm. 100% B |
|  | 20.1 mm. 100% A |
| Run Time | 28 min. |
| Flow Rate | 1.5 mL/min |
| UV Detector | 230 nm |
| Injection Volume | 20 µL |
| Column Temperature | 30° C. |

ACN: acetonitrile
PCA: perchloric acid

Gel Preparation

One of ordinary skill in the art would understand that the process below can be modified, if necessary, in order to be scaled up.

The following laboratory-scale process has been used to manufacture gels formulations of the pharmaceutical compositions of the present invention. (During this process, the vessel was open part of the time to allow insertion and operation of mixing blades attached to an overhead stirrer. To compensate for alcohol evaporation, a 2.0% overage of this solvent was used.)

1. Solvents and emollients were added to a suitable vessel. A magnetic stir bar was added, the vessel was sealed and placed on a stir plate. Mixing continued until the liquids are homogenous.

2. The seal was removed, BHT was added, and the seal was replaced. The solution was mixed until the antioxidant dissolved.

3. The seal was removed, the acid was added, and the seal was replaced. The solution was mixed until homogeneous. If citric acid was used, the powder was added directly to the vessel. If phosphoric acid was used, it was weighed into a small beaker then rinsed into the vessel with some reserved ethanol.

4. The seal was removed, compound (II) was added (for active formulations only), and the seal was replaced. The solution was mixed until the active dissolved.

5. The seal was removed, the stir bar carefully removed, and a propeller mixer blade attached to an overhead stirrer was inserted. The mixing speed was adjusted to form a good vortex without excessive cavitation or splashing.

6. The Klucel MF PH was slowly added into the vortex to disperse the polymer. Mixing speed was adjusted as the formulation thickened to maintain good mixing of the drug product without excessive aeration. The vessel was partially covered to minimize evaporation.

7. Approximately 20-30 minutes after adding the polymer, thickening occurred to the point where the propeller blade was not sufficient to keep all of the formulation mixing smoothly. The propeller blade was carefully removed and the formulation was drained off the blade into the vessel (this was assisted with spatulation).

8. A suitable anchor blade attached to an overhead stirrer was inserted and mixing continued at a suitable speed. The vessel was partially covered to minimize evaporation.

9. Approximately 2 hours after adding the polymer, the gel was homogeneous with a slightly mottled appearance. To minimize evaporation while the polymer continued to swell, the anchor stirrer was carefully removed (allowing the gel to drain off into the vessel) and the vessel was sealed.

10. The vessel was stored at room temperature protected from light for 12-18 hours. After storage, the gel was remixed for an additional 15 minutes. After final mixing was completed, the gel was filled into a suitable container.

Results

In neutral ethanol at room temperature, compound (II) degrades by approximately 50% in 24 hours.

Six active batches were prepared at the 350 g scale. The citric acid level was reduced slightly so that the pH would move closer to 4.0. Their compositions and initial results are summarized in Tables 2A-2B and Tables 3A-3B, respectively.

TABLE 2A

Compositions A, B, C and D (all values in % w/w, dehydrated ethanol USP added to bring total to 100%)

| | A | B | C | D |
|---|---|---|---|---|
| Compound (II) | 1.0 | 1.0 | 1.0 | 1.0 |
| Propylene glycol, USP | 15.0 | — | 15.0 | — |
| Glycerin, USP | 10.0 | — | 10.0 | — |
| diethylene glycol monoethyl ether, USP | — | 25.0 | — | 25.0 |
| Hexylene glycol, NF | 12.0 | 12.0 | 12.0 | 12.0 |
| Diisopropyl adipate | 4.0 | 4.0 | 4.0 | 4.0 |
| Oleyl alcohol, NF | 5.0 | 5.0 | 5.0 | 5.0 |
| BHT, NF | 0.1 | 0.1 | 0.1 | 0.1 |
| Citric acid (anhydrous), USP | 0.045 | 0.045 | — | — |
| Phosphoric acid (85%), USP | — | — | 0.015 | 0.015 |
| Klucel MF PH | 2.0 | 2.0 | 2.0 | 2.0 |

TABLE 2B

Compositions E and F (all values in % w/w)

| | E | F |
|---|---|---|
| Compound (II) | 0.1 | 0.5 |
| Propylene glycol, USP | 15.0 | 15.0 |
| Glycerin, USP | 10.0 | 10.0 |
| Diethylene glycol monoethyl ether, USP | 0.0 | 0.0 |
| Hexylene glycol, NF | 12.0 | 12.0 |
| Diisopropyl adipate | 4.0 | 4.0 |
| Oleyl alcohol, NF | 5.0 | 5.0 |
| BHT, NF | 0.1 | 0.1 |
| Citric acid (anhydrous), USP | 0.045 | 0.045 |
| Phosphoric acid (85%), USP | 0 | 0 |
| Klucel MF PH | 2.0 | 2.0 |
| Dehydrated alcohol (ethanol), USP | 51.755 | 51.355 |

TABLE 3A

Initial results for compositions in Table 2A

| | A | B | C | D |
|---|---|---|---|---|
| Compound (II), % w/w | 0.994 | 0.995 | 0.996 | 0.995 |
| BHT assay, % w/w | 0.099 | 0.099 | 0.102 | 0.101 |
| pH | 3.75 | 3.92 | 3.95 | 3.89 |
| Viscosity, cP | 18,800 | 20,000 | 17,600 | 21,200 |
| Appearance | Conforms[1] | Conforms[1] | Conforms[1] | Conforms[1] |

[1]Clear or translucent colorless viscous liquid

TABLE 3B

Initial results for compositions in Table 2B

| Property | E | F |
|---|---|---|
| SHP-141 assay, % w/w | 0.100 | 0.499 |
| BHT assay, % w/w | 0.099 | 0.099 |
| pH | 3.80 | 3.70 |
| Viscosity, cP | Not tested | 24,532 |
| Appearance | Conforms[1] | Conforms[1] |

[1]Clear to translucent colorless viscous liquid.

The results of a 6-month study of stability of formulations A, B and C are presented below in Table 4 through Table 8.

TABLE 4

Stability of Compound (II) gels after 2 weeks of storage at 40° C.

| | A | B | C |
|---|---|---|---|
| Compound (II), % initial | 98.3 | 98.5 | 98.1 |
| BHT, % initial | 100.4 | 100.1 | 99.7 |
| pH | 3.85 | 3.79 | 3.95 |
| Viscosity, cP | 16,800 | 17,600 | 16,000 |
| Appearance | Conforms[1] | Conforms[1] | Conforms[1] |

[1]Clear or translucent colorless viscous liquid

TABLE 5

Stability results for Compound (II) gels after 1 month of storage at 2-8 and 25° C.

|  | A | B | C |
|---|---|---|---|
| Compound (II), % initial |  |  |  |
| 1 month, 25° C. | 98.4 | 98.5 | 98.2 |
| 1 month, 2-8° C. | 99.9 | 99.8 | 99.4 |
| BHT assay, % initial |  |  |  |
| 1 month, 25° C. | 99.8 | 100.3 | 99.8 |
| 1 month, 2-8° C. | 99.7 | 99.9 | 99.6 |
| pH |  |  |  |
| 1 month, 25° C. | 3.92 | 3.80 | 3.90 |
| 1 month, 2-8° C. | 3.84 | 3.97 | 3.99 |
| Viscosity, cP |  |  |  |
| 1 month, 25° C. | 19,200 | 22,400 | 20,000 |
| 1 month, 2-8° C. | 20,400 | 22,000 | 21,600 |
| Appearance |  |  |  |
| 1 month, 25° C. | Conforms[1] | Conforms[1] | Conforms[1] |
| 1 month, 2-8° C. | Conforms[1] | Conforms[1] | Conforms[1] |

[1]Clear or translucent colorless viscous liquid

TABLE 6

Stability of Compound (II) gels after 2 months of storage at 2-8 and 25° C.

|  | A | B | C |
|---|---|---|---|
| Compound (II), % initial |  |  |  |
| 2 month, 25° C. | 97.1 | 96.9 | 96.5 |
| 2 month 2-8° C. | 99.1 | 98.8 | 98.6 |
| BHT assay, % initial |  |  |  |
| 2 month, 25° C. | 99.5 | 99.7 | 99.5 |
| 2 month 2-8° C. | 99.8 | 99.8 | 99.5 |
| pH |  |  |  |
| 2 month, 25° C. | 3.85 | 3.91 | 4.02 |
| 2 month 2-8° C. | 3.83 | 3.88 | 3.94 |
| Viscosity, cP |  |  |  |
| 2 month, 25° C. | 20,400 | 23,200 | 22,800 |
| 2 month 2-8° C. | 20,800 | 21,200 | 23,200 |
| Appearance |  |  |  |
| 2 month, 25° C. | Conforms[1] | Conforms[1] | Conforms[1] |
| 2 month 2-8° C. | Conforms[1] | Conforms[1] | Conforms[1] |

[1]Clear or translucent colorless viscous liquid

TABLE 7

Stability of Compound (II) gels after 3 months of storage at 2-8 and 25° C.

|  | A | B | C |
|---|---|---|---|
| Compound (II), % initial |  |  |  |
| 3 months, 25° C. | 96.4 | 96.1 | 95.6 |
| 3 months, 2-8° C. | 98.6 | 98.3 | 97.5 |
| BHT assay, % initial |  |  |  |
| 3 months, 25° C. | 99.7 | 99.7 | 99.6 |
| 3 months, 2-8° C. | 99.5 | 99.4 | 99.9 |
| pH |  |  |  |
| 3 months, 25° C. | 3.95 | 3.81 | 3.96 |
| 3 months, 2-8° C. | 3.82 | 3.84 | 4.05 |
| Viscosity, cP |  |  |  |
| 3 months, 25° C. | 24,000 | 24,400 | 24,000 |
| 3 months, 2-8° C. | 22,800 | 23,200 | 24,800 |
| Appearance |  |  |  |
| 3 months, 25° C. | Conforms[1] | Conforms[1] | Conforms[1] |
| 3 months, 2-8° C. | Conforms[1] | Conforms[1] | Conforms[1] |

[1]Clear or translucent colorless viscous liquid

TABLE 8

Stability of Compound (II) gels after 6 months of storage at 2-8 and 25° C.

|  | A | B | C |
|---|---|---|---|
| Compound (II), % initial |  |  |  |
| 6 month, 25° C. | 95.0 | 94.5 | 93.4 |
| 6 month 2-8° C. | 97.9 | 97.7 | 96.9 |
| BHT assay, % initial |  |  |  |
| 6 month, 25° C. | 99.4 | 99.2 | 99.0 |
| 6 month 2-8° C. | 99.3 | 99.4 | 99.3 |
| pH |  |  |  |
| 6 month, 25° C. | 3.87 | 3.89 | 4.01 |
| 6 month 2-8° C. | 3.85 | 3.94 | 3.95 |
| Viscosity, cP |  |  |  |
| 6 month, 25° C. | 23,600 | 23,600 | 25,200 |
| 6 month 2-8° C. | 22,000 | 22,400 | 23,600 |
| Appearance |  |  |  |
| 6 month, 25° C. | Conforms[1] | Conforms[1] | Conforms[1] |
| 6 month 2-8° C. | Conforms[1] | Conforms[1] | Conforms[1] |

[1]Clear or translucent colorless viscous liquid

The results of a 3-month study of stability of formulations E and F are presented below in Table 9.

TABLE 9

Stability of formulations E and F after 3 months of storage

| Property | E | F |
|---|---|---|
| SHP-141 assay, % initial |  |  |
| 3 month, 25° C. | 100.1 | 99.0 |
| 3 month, 2-8° C. | 100.6 | 99.7 |
| BHT assay, % initial |  |  |
| 3 month, 25° C. | 99.3 | 103.3 |
| 3 month, 2-8° C. | 100.6 | 103.8 |
| pH |  |  |
| 3 month, 25° C. | 3.90 | 4.00 |
| 3 month, 2-8° C. | 3.90 | 4.00 |
| Viscosity, cP |  |  |
| 3 month, 25° C. | 20,800 | 25,435 |
| 3 month, 2-8° C. | 21,550 | 25,288 |
| Appearance |  |  |
| 3 month, 25° C. | Conforms[1] | Conforms[1] |
| 3 month, 2-8° C. | Conforms[1] | Conforms[1] |

[1]Clear to translucent colorless viscous liquid.

The results of a 6-month study of stability of formulation F are presented below in Table 10.

TABLE 10

Stability of formulation F after 6 months of storage

| Property | F |
|---|---|
| SHP-141 assay, % initial | |
| 6 month, 25° C. | 99.5 |
| 6 month, 2-8° C. | 100.5 |
| BHT assay, % initial | |
| 6 month, 25° C. | 99.5 |
| 6 month, 2-8° C. | 100.3 |
| pH | |
| 6 month, 25° C. | 4.00 |
| 6 month, 2-8° C. | 3.80 |
| Viscosity, cP | |
| 6 month, 25° C. | 25,448 |
| 6 month, 2-8° C. | 24,042 |
| Appearance | |
| 6 month, 25° C. | Conforms[1] |
| 6 month, 2-8° C. | Conforms[1] |

[1]Clear to translucent colorless viscous liquid.

The results of a 6-month study of stability of formulation E are presented in Tables 11 and 12.

TABLE 11

Stability of formulation E after 6 months of storage at 5° C.

| Parameter | E |
|---|---|
| Assay | 102.0 |
| BHT | 98.2 |
| pH | 3.9 |
| Viscosity | 21240 cP |

TABLE 12

Stability of formulation E after 6 months of storage at 25° C. and 60% relative humidity

| Parameter | E |
|---|---|
| Assay | 99.3 |
| BHT | 97.3 |
| pH | 3.9 |
| Viscosity | 22480 cP |

The results of a 12-month study of stability of formulation A and F are presented in Tables 13 and 14.

TABLE 13

Stability of formulations A and F after 12 months of storage at 5° C.

| Parameter | F | A |
|---|---|---|
| Assay | 102.5 | 100.9 |
| BHT | 99.2 | 99.2 |
| pH | 3.8 | 3.8 |
| Viscosity | 29910 cP | 23750 cP |

TABLE 14

Stability of formulations A and F after 12 months of storage at 25° C. and 60% relative humidity

| Parameter | F | A |
|---|---|---|
| Assay | 99.2 | 94.4 |
| BHT | 97.9 | 97.1 |
| pH | 3.9 | 3.8 |
| Viscosity | 27150 cP | 25110 cP |

Conclusions

In neutral ethanol at room temperature, compound (II) degrades by approximately 50% in 24 hours.

It has now been discovered that compound (II) could be successfully formulated in a acidified nonaqueous gel with acceptable cosmesis. Under the typical temperature conditions in a refrigerated storage (2-8° C.), the formulation's saturation solubility for compound (II) was approximately 1.6% w/w. There was no significant change in appearance, pH, or BHT assay for 1% compound (II) gels after storage at 2-8° C. (3 months), 25° C. (3 months), or 40° C. (2 weeks). The viscosity for vehicle and active gels showed a slight increase on storage at 2-8 or 25° C., which is typical for nonaqueous Klucel gels. The slight increase in viscosity did an affect pourability or spreadability (assessed for vehicle gels, only). The compound (II) concentration decreased on average of by 1.9 or 4.0% after three months storage at 2-8 or 25° C., respectively. Exposure to laboratory light for up to five days did not significantly affect the assay values for compound (II). All samples passed identity and were clear, colorless, viscous gel solutions. All assay, impurity, and BHT sample results are an average of three replicate preparations, top, middle, and bottom, from single bottles.

Example 2

Formulation Kit Examples

Topical formulations of compound (II) were prepared from a kit that contains the following components: a vial of compound (II) powder, a vial of solvent, and a container of gel concentrate. All three of these components are stable at controlled room temperature. At the time of dispensing, the contents of the solvent vial were added to the compound (II) vial to dissolve the compound. After compound (II) had been solubilized, the solution was added to the gel concentrate and then mixed with a suitable implement (i.e., spatula) until homogeneous.

Three-compartment kit examples for two formulations are described below in Table 15 and Table 16.

TABLE 15

| | Example Kit A | | |
|---|---|---|---|
| Compound | Amount in Container 1, % w/w | Amount in Container 2, % w/w | Amount in Container 3, % w/w |
| Compound (II) | 100 | — | — |
| Ethanol (190 proof) | — | 84.95 | — |
| Propylene Glycol | — | 15.0 | 15.2 |
| Citric Acid | — | 0.045 | 0.046 |
| Hexylene Glycol | — | — | 18.3 |
| Glycerin | — | — | 15.2 |
| Diisopropyl Adipate | — | — | 6.10 |

TABLE 15-continued

Example Kit A

| Compound | Amount in Container 1, % w/w | Amount in Container 2, % w/w | Amount in Container 3, % w/w |
|---|---|---|---|
| Oleyl Alcohol | — | — | 7.61 |
| BHT | — | — | 0.15 |
| Klucel MF PH | — | — | 3.05 |
| Ethanol (200 proof) | — | — | 34.3 |

For 30 grams of gelled solution with a final compound (II) concentration of 1%, the following weights of each component were used: 0.3 g of compound (II), 10.0 g of solvent, and 19.7 g of gel concentrate.

TABLE 16

Example Kit B

| Compound | Amount in Container 1, % w/w | Amount in Container 2, % w/w | Amount in Container 3, % w/w |
|---|---|---|---|
| Compound (II) | 100 | — | — |
| Ethanol (200 proof) | — | 74.95 | 34.9 |
| Benzyl Alcohol | — | 25.0 | — |
| Citric Acid | — | 0.045 | 0.046 |
| Propylene Glycol | — | — | 20.3 |
| Hexylene Glycol | — | — | 16.2 |
| Glycerin | — | — | 13.5 |
| Diisopropyl Adipate | — | — | 5.41 |
| Oleyl Alcohol | — | — | 6.76 |
| BHT | — | — | 0.135 |
| Klucel MF PH | — | — | 2.70 |

For 30 grams of gelled solution with a final concentration of compound (II) of 1% using Formulation B, the following weights of each component were used: 0.3 g of compound (II), 7.5 g of solvent, and 22.2 g of gel concentrate.

For both examples above, a homogeneous gelled formulation was obtained after less than 4 minutes of mixing. Compound (II) formulations prepared from a three compartment kit were stable for at least one month at controlled room temperature or in the refrigerator.

Example 3

Evaluation of the Percutaneous Absorption of Compound (II) In Vitro Using the Franz Human Skin Finite Dose Model In this example, solutions A and B, as described above, ewre used. Control solution ("Ctrl") was a 1% by weight solution of compound (II) in DMSO.

Three test formulations containing compound (II)—A, B and Ctrl were tested on three replicate sections from two different ex vivo human trunk skin donors, for the percutaneous absorption of compound (II), and for the appearance of compound (III) depicted below, Methylparaben, and 4-OH Benzoic acid over a 24 hour dose period. At preselected times after dose application, the dermal receptor solution was removed in its entirety, replaced with fresh receptor solution, and an aliquot saved for subsequent analysis. In addition, the stratum corneum, epidermis and dermis were recovered and evaluated for drug content. The samples were analyzed for compound (II), compound of structural formula (III)

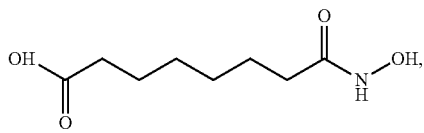

Methylparaben

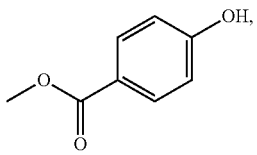

and 4-OH Benzoic acid content by High Performance Liquid Chromatography (HPLC).

Materials and Methods

The in vitro Franz human skin finite dose model has proven to be a valuable tool for the study of percutaneous absorption and the determination of the pharmacokinetics of topically applied drugs. The model uses human ex vivo cadaver or surgical skin mounted in specially designed diffusion cells that allow the skin to be maintained at a temperature and humidity that match typical in vivo conditions. A finite dose (e.g. 4-7 mg/cm$^2$) of formulation is applied to the outer surface of the skin and drug absorption is measured by monitoring its rate of appearance in the receptor solution bathing the inner surface of the skin. Data defining total absorption, rate of absorption, as well as skin content can be accurately determined in this model. The method has historic precedent for accurately predicting in vivo percutaneous absorption kinetics.

Compound (II) degrades to less potent compounds, namely compound (III) and Methylparaben. Compound (III) may undergo further degradation to suberic acid. Methylparaben may undergo degradation to 4-OH Benzoic acid. In this study compound (II), compound (III), Methylparaben and 4-OH Benzoic acid were quantified in the collected samples.

Study Skin Preparation

Percutaneous absorption was measured using the in vitro Franz human skin finite dose technique. Ex vivo, human trunk skin without obvious signs of skin disease, obtained within 24-48 hours of death, was used in this study. It was dermatomed, prepared for cryopreservation, sealed in a water impermeable plastic bag, and stored at about −70° C. until the day of the experiment. Prior to use it was thawed in about 37° C. water, then rinsed in water to remove any adherent blood or other material from the surface.

Skin from a single donor was cut into multiple smaller sections large enough to fit on static 1.0 cm$^2$ Franz diffusion cells. The dermal chamber was filled to capacity with a reservoir solution of phosphate-buffered isotonic saline (PBS), pH 7.4±0.1, and the epidermal cell (chimney) left open to ambient laboratory conditions.

All cells were mounted in a diffusion apparatus in which the dermal bathing solution was stirred magnetically at approximately 600 RPM and the skin surface temperature maintained at 32.0° C.±1.0° C.

To assure the integrity of each skin section, its permeability to tritiated water was determined before application of the test products. Following a brief (0.5-1 hour) equilibrium period, $^3H_2O$ (NEN, Boston, Mass., sp. Act. apprx. 0.5 μCi/mL) was layered across the top of the skin so that the entire exposed surface was covered (approximately 200-500 μL). After 5 minutes the $^3H_2O$ aqueous layer was removed. At 30 minutes the receptor solution was collected and analyzed for radioactive content by liquid scintillation counting. Skin specimens in which absorption of $^3H_2O$ was less than 1.56 μL-equ/cm² were considered acceptable.

Dosing and Sample Collection

Just prior to dosing, a pre-dose sample was taken and the reservoir solution was replaced with a fresh solution of 0.1×PBS with 0.1% Volpo and 0.05% Citric acid (nominal pH 6.0). The chimney was removed from the Franz Cell to allow full access to epidermal the surface of the skin. All formulations were then applied to the skin sections using a positive displacement pipette set to deliver 5 μL formulation/cm². The dose was evenly distributed onto the skin using a glass rod. The rod was retained for analysis to correct the applied dose. Five to ten minutes after application the chimney portion of the Franz Cell was replaced. At preselected times after dosing, (6, 12, and 24 hours) the reservoir solution was removed in its entirety, replaced with fresh reservoir solution, and a predetermined volume aliquot saved for subsequent analysis.

Spare cells were available which were not dosed but used to evaluate for the appearance of substances diffusing out of the skin that might interfere with the analytic method.

After the last sample was collected, the surfaces were washed twice (0.5 mL volume each) with Ethanol with 0.05% Citric Acid to collect un-absorbed formulation from the surface of the skin. Following the wash, the skin was tape stripped to remove the stratum corneum. The tape strips were extracted overnight in neat acetonitrile. The skin was then removed from the chamber, split into epidermis and dermis. Each was extracted overnight in a mixture of Ethanol and 0.05% citric acid over wet ice.

Analytical Methods

Samples were assayed using an HPLC/MS and/or HPLC/UV.

Results

Results are presented in Table 17 and Table 18, below. (In Tables 17 and 18, an entry of "0" means that the parameter was below lower limit of quantification.)

TABLE 17

Total Absorption and Mass Balance Results Across Skin Donors: Percutaneous Absorption and Penetration of Compound (II) Through ex vivo Human Trunk Skin Over 24 Hours (Mean ± SE as Percent of Applied Dose and Total Mass (μg/cm²).)

|  | 1% Compound (II) Gel Formulation A of Table 3 | 1% Compound (II) Gel Formulation B of Table 3 | 1% Compound (II) Solution (DMSO) (Ctrl) |
|---|---|---|---|
| Total Absorption (μg/cm2) | 0.284 ± 0.028 | 0 | 0.296 ± 0.098 |
| Dermis (μg/cm2) | 0 | 0 | 0 |
| Epidermis (μg/cm2) | 0.259 ± 0.074 | 0.151 ± 0.004 | 0.429 ± 0.035 |

TABLE 17-continued

Total Absorption and Mass Balance Results Across Skin Donors: Percutaneous Absorption and Penetration of Compound (II) Through ex vivo Human Trunk Skin Over 24 Hours (Mean ± SE as Percent of Applied Dose and Total Mass (μg/cm²).)

|  | 1% Compound (II) Gel Formulation A of Table 3 | 1% Compound (II) Gel Formulation B of Table 3 | 1% Compound (II) Solution (DMSO) (Ctrl) |
|---|---|---|---|
| Stratum Corneum (μg/cm2) | 0.048 ± 0.022 | 0.039 ± 0.039 | 0.016 ± 0.016 |
| Surface Wash (μg/cm2) | 22.12 ± 3.938 | 31.94 ± 0.313 | 10.01 ± 0.189 |
| Total Absorption (%) | 0.594 ± 0.060 | 0 | 0.600 ± 0.199 |
| Dermis (%) | 0 | 0 | 0 |
| Epidermis (%) | 0.542 ± 0.158 | 0.325 ± 0.004 | 0.870 ± 0.072 |
| Stratum Corneum (%) | 0.101 ± 0.045 | 0.087 ± 0.087 | 0.032 ± 0.032 |
| Surface Wash (%) | 46.28 ± 8.538 | 68.56 ± 1.957 | 20.29 ± 0.340 |
| Total Recovery (%) | 47.52 ± 8.592 | 68.97 ± 2.048 | 21.79 ± 0.498 |

TABLE 18

Compound (II) Total Absorption Results Across Donors Percutaneous: Absorption of Compound (II) Through ex vivo Human Trunk Skin Over 24 Hours From a Single Application. (Mean ± SE as Total Mass (μg/cm²) and Percent of Applied Dose.)

| Test Article | Total Absorption (μg/cm2) | Total Absorption (%) |
|---|---|---|
| 1% Compound (II) Gel, Formulation A of Table 3 | 0.284 ± 0.028 | 0.594 ± 0.060 |
| 1% Compound (II) Gel, Formulation B of Table 3 | 0 | 0 |
| 1% Compound (II) Solution (DMSO), Ctrl | 0.296 ± 0.098 | 0.600 ± 0.199 |

Conclusion

Using the in vitro finite dose model, the data demonstrates that compound (II) penetrates into and through ex vivo human skin, from formulations A and Ctrl, but not from formulation B (see Table 2 for the formulations A and B).

The penetration profile for compound (II) suggests that virtually all the percutaneous absorption through the skin occurred within 5 hours of dose application from formulations A and Ctrl, with no compound (II) being seen in the reservoir solution from formulation B. The majority of the detectable compound (II) was found in the surface wash (about 20%-69%) followed by the epidermis (about 0.3%-0.9%).

The data further indicate that all of the degradation products to be quantified (compound (III), Methylparaben (structural formula (IV)), and 4-OH Benzoic acid) were observed to be present in the majority of the samples.

Further, degree of degradation was observed to be formulation dependent with more degradation being seen in the samples dosed with formulation Ctrl, followed by formulation A and formulation B.

Overall mass balance (based on the amount of compound (II) dose) as the sum across all measured compounds demonstrated about 71% recovery from the skin sections dosed with formulation B, about 55% from the skin sections dosed with formulation A, and about 51% from the skin sections dosed with formulation Ctrl. The unaccountable dose may represent other degradation products which were not quantified, or binding of selected compounds to the tissue or chamber system surfaces.

While this invention has been particularly shown and described with references to example embodiments thereof, it will be understood by those skilled in the art that various changes in form and details may be made therein without departing from the scope of the invention encompassed by the appended claims.

The invention claimed is:

1. A method of treating basal cell carcinoma in a subject in need thereof, said method comprising cutaneously administering to the subject a therapeutically effective amount of a pharmaceutical composition comprising
an active pharmaceutical ingredient (API) compound represented by the following structural formula

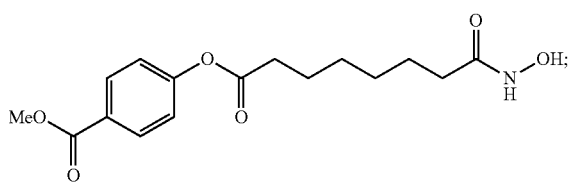 [SMILES: COC(=O)c1ccc(OC(=O)CCCCCCC(=O)NO)cc1]

at least one acidifying agent which comprises citric acid; and
a vehicle base comprising at least one pharmaceutically acceptable non-aqueous solvent,
wherein the pharmaceutical composition has a measured pH of from about 3 to about 5;
the API is present in an amount of about 0.5 to 5.0% (w/w); and
the at least one non-aqueous solvent comprises ethanol.

2. The method of claim 1 wherein the pharmaceutical composition further comprises at least one humectant.

3. The method of claim 2, wherein the at least one humectant is selected from the group consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

4. The method of claim 2, wherein the at least one humectant is selected from glycerin and hexylene glycol.

5. The method of claim 1 wherein the pharmaceutical composition further comprises at least one emollient.

6. The method of claim 5 wherein the at least one emollient of the pharmaceutical composition is selected from the group consisting of diisopropyl adipate, isopropyl myristate, isopropyl palmitate, cetearyl octonoate, isopropyl isostearate, myristyl lactate, octyldodecanol, oleyl alcohol, a mineral oil, petrolatum, a vegetable oil, PPG-15 stearyl ether, PEG-4 dilaurate, lecithin, lanolin, lanolin alcohol, polyoxyl 75 lanolin, cholesterol, cetyl esters wax, cetostearyl alcohol, glyceryl monostearate, triglycerides of capric and caprylic acids, dimethicone, and cyclomethicone.

7. The method of claim 5 wherein the at least one emollient of the pharmaceutical composition is selected from diisopropyl adipate and oleyl alcohol.

8. The method of claim 1 wherein the pharmaceutical composition further comprises at least one humectant and at least one emollient.

9. The method of claim 8 wherein the at least one humectant of the pharmaceutical composition is selected from glycerin and hexylene glycol and wherein the at least one emollient is selected from diisopropyl adipate and oleyl alcohol.

10. The method of claim 1 wherein the pharmaceutical composition further comprises at least one skin permeation enhancer.

11. The method of claim 10 wherein the at least one permeation enhancer of the pharmaceutical composition is selected from one or more of oleyl alcohol, propylene glycol, and ethanol.

12. The method of claim 1 wherein the pharmaceutical composition further comprises at least one gelling agent.

13. The method of claim 12, wherein the at least one gelling agent of the pharmaceutical composition is a hydroxypropylcellulose.

14. The method of claim 1 wherein the pharmaceutical composition further comprises at least one antioxidant.

15. The method of claim 14, wherein the antioxidant of the pharmaceutical composition is selected from the group consisting of alpha tocopherol, beta tocopherol, delta tocopherol, gamma tocopherol, tocopherols, ascorbic acid, ascorbyl palmitate, butylated hydroxyanisol, butylated hydroxytoluene, fumaric acid, malic acid, methionine, propyl gallate, sodium ascorbate, sodium metabisulfate, sodium thiosulfate, and sodium bisulfate.

16. The method of claim 14, wherein the antioxidant is the butylated hydroxytoluene.

17. The method of claim 1 wherein the pharmaceutical composition comprises at least 1.0% by weight of the API.

18. The method of claim 1, wherein the ethanol is present in an amount of about 50% (w/w); and wherein the measured pH of the pharmaceutical composition is from about 3 to about 4.

19. The method of claim 17, wherein the ethanol is present in an amount of about 50% (w/w); and wherein the measured pH of the pharmaceutical composition is from about 3 to about 4.

* * * * *